(12) United States Patent
Fukase et al.

(10) Patent No.: US 9,831,413 B2
(45) Date of Patent: Nov. 28, 2017

(54) ULTRASOUND PROBE AND FLEXIBLE SUBSTRATE USED IN ULTRASOUND PROBE

(71) Applicant: KONICA MINOLTA, INC., Tokyo (JP)

(72) Inventors: Hirokazu Fukase, Kanagawa (JP); Kouji Ooura, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 563 days.

(21) Appl. No.: 14/161,576

(22) Filed: Jan. 22, 2014

(65) Prior Publication Data

US 2014/0132114 A1    May 15, 2014

Related U.S. Application Data

(63) Continuation of application No. PCT/JP2012/004938, filed on Aug. 3, 2012.

(30) Foreign Application Priority Data

Aug. 5, 2011  (JP) ................................ 2011-171566

(51) Int. Cl.
    *H01L 41/047*    (2006.01)
    *B06B 1/06*      (2006.01)
    *A61B 8/00*      (2006.01)

(52) U.S. Cl.
    CPC ............ *H01L 41/0475* (2013.01); *B06B 1/06* (2013.01); *B06B 1/0622* (2013.01); *A61B 8/4461* (2013.01)

(58) Field of Classification Search
    CPC ....... H04R 17/00; B06B 1/0603; G10K 11/30
    USPC .......................... 310/322, 334, 335; 600/459
    See application file for complete search history.

(56) References Cited

U.S. PATENT DOCUMENTS

| 6,396,199 | B1  | 5/2002  | Douglas et al. |
| 7,375,286 | B2  | 5/2008  | Honjo |
| 8,547,799 | B2* | 10/2013 | Rhim ....................... A61B 8/00 367/155 |

(Continued)

FOREIGN PATENT DOCUMENTS

| CN | 101052266 A | 10/2007 |
| JP | 05-244693 A | 9/1993 |

(Continued)

OTHER PUBLICATIONS

English Transaltion of JP 2009099837.*

(Continued)

*Primary Examiner* — Bryan Gordon
(74) *Attorney, Agent, or Firm* — Holtz, Holtz & Volek PC

(57) ABSTRACT

An ultrasound probe of the present disclosure includes an ultrasound element unit 1, to which a flexible substrate 7 is connected, the flexible substrate 7 including lamination of a ground layer 7e and a signal layer 7a via an insulation layer 7c. The flexible substrate 7 includes a bending part and a flat part. The signal layer 7a includes a linear first signal line and a linear second signal line that are adjacent to each other. The ground layer 7e at the bending part includes a linear first ground line and a linear second ground line that are adjacent to each other. The first signal line and the first ground line are opposed to each other, and the second signal line and the second ground line are opposed to each other.

11 Claims, 8 Drawing Sheets

(56) References Cited

U.S. PATENT DOCUMENTS

| | | | |
|---|---|---|---|
| 2004/0167405 A1* | 8/2004 | Sudo | B06B 1/0622 600/459 |
| 2007/0227764 A1 | 10/2007 | Honjo | |
| 2010/0176688 A1* | 7/2010 | Jin | A61B 8/00 310/327 |
| 2011/0121687 A1* | 5/2011 | Aoki | B06B 1/0677 310/334 |
| 2011/0139493 A1* | 6/2011 | Sumida | G02F 1/13452 174/254 |
| 2011/0288416 A1* | 11/2011 | Ishidai | B06B 1/064 600/459 |
| 2012/0022378 A1* | 1/2012 | Ishidai | B06B 1/0622 600/459 |

FOREIGN PATENT DOCUMENTS

| | | |
|---|---|---|
| JP | 06-038962 A | 2/1994 |
| JP | 2003-518394 A | 6/2003 |
| JP | 2006-294929 A | 10/2006 |
| JP | 2007-281000 A | 10/2007 |
| JP | 2007-288704 A | 11/2007 |
| JP | 2010-219262 A | 9/2010 |
| JP | 2010-278132 A | 12/2010 |

OTHER PUBLICATIONS

Chinese Office Action (and English translation thereof) dated Apr. 3, 2015, issued in counterpart Chinese Application No. 201280036862.9.

English translation of International Search Report, dated Aug. 28, 2012, for corresponding International application No. PCT/JP2012/004938, 2 pages.

\* cited by examiner

ULTRASOUND PROBE AND FLEXIBLE SUBSTRATE USED IN ULTRASOUND PROBE

This is a continuation of International Application No. PCT/JP2012/004938, with an international filing date of Aug. 3, 2012, which claims priority of Japanese Patent Application No. 2011-171566, filed on Aug. 5, 2011, the contents of which are hereby incorporated by reference.

FIELD OF THE INVENTION

The present disclosure relates to an ultrasound probe capable of reducing connection failure of a transmission/reception signal and a flexible substrate used for such an ultrasound probe.

DESCRIPTION OF THE RELATED ART

Conventionally known ultrasound probes are configured to mechanically swing an ultrasound element in an enclosure filled with acoustic coupling solution as described in Patent Document 1, for example. This ultrasound element transmits/receives ultrasound waves, and an ultrasound diagnosis apparatus main body processes the ultrasound waves, whereby two-dimensional images or three-dimensional images are generated.

FIG. 12 schematically shows the structure of a conventional ultrasound probe 100. An ultrasound element unit 101 is connected to an ultrasound diagnosis apparatus main body (not illustrated) via a probe cable 102. An enclosure 103 storing the ultrasound element unit 101 is filled with acoustic coupling solution 104 so that the ultrasound element unit 101 is soaked in the acoustic coupling solution 104. The ultrasound element unit 101 is configured to mechanically swing about a set rotary axle.

Another known ultrasound element includes the lamination of a piezoelectric element, a flexible substrate for signal extraction and a backing material (see Patent Document 2, for example).

FIG. 13 schematically shows the ultrasound element unit 101. The ultrasound element unit 101 includes: a piezoelectric element 105; a flexible substrate for signals and grounding 106 to transmit electrical signals for transmission and reception with respect to the piezoelectric element 105; and a backing material 107 attached to the piezoelectric element 105 on the opposite side of an ultrasound waves emission face of the piezoelectric element 105. The piezoelectric element 105 is divided into several tens to several hundreds of elements by dicing, for example. The flexible substrate for signals and grounding 106 is formed with a conductive patterning corresponding to these elements. As shown in FIG. 12, the ultrasound element unit 101 and the probe cable 102 are connected at the flexible substrate for signals and grounding 106, and the flexible substrate for signals and grounding 106 is designed for bending. The bending part of the flexible substrate for signals and grounding 106 is fixed to the backing material 107 or is fixed in the vicinity of the piezoelectric element 105 by another component.

The flexible substrate for signals and grounding 106 used for a conventional ultrasound probe typically includes the lamination of an I/O signal layer and a ground layer. Then, the I/O signal layer includes a conductor provided with patterning corresponding to the ultrasound elements divided into several tens to several hundreds of elements, and the ground layer is provided with patterning to let the ultrasound elements divided into several tens to several hundreds of elements have common electrical potential (see Patent Document 3, for example).

The piezoelectric element 105 of the ultrasound element unit 101 receives a driving signal from an ultrasound diagnosis apparatus main body (not illustrated) via the probe cable 102 and the flexible substrate for signals and grounding 106. The piezoelectric element 105 converts the driving signal from the ultrasound diagnosis apparatus main body into ultrasound waves, and the ultrasound waves are applied to a subject (not illustrated). The ultrasound waves reflected from the subject are received and converted into electrical signals by the piezoelectric element 105, which are then sent to the ultrasound diagnosis apparatus main body via the flexible substrate for signals and grounding 106 and the probe cable 102. The ultrasound diagnosis apparatus main body processes the electrical signals based on the ultrasound waves reflected from the subject, whereby a two-dimensional image can be acquired. When the ultrasound element unit 101 mechanically swings, the ultrasound diagnosis apparatus main body can generate a three-dimensional image in a similar manner.

The flexible substrate for signals and grounding 106 is required to have flexibility so as to prevent a break of a signal line due to mechanical load generated from the swinging of the ultrasound element unit 101. To this end, a conventional flexible substrate for signals and grounding includes a ground layer having a plurality of small round holes bored therein to be a mesh form, thus reducing the bending load applied to the bending part (see Patent Document 4, for example).

Patent Document 1: Japanese Patent Application Publication No. H6-38962
Patent Document 2: Japanese Patent Application Publication No. H5-244693
Patent Document 3: Japanese Patent Application Publication No. 2003-518394
Patent Document 4: Japanese Patent Application Publication No. 2006-294929

SUMMARY

The conventional configurations have the ground layer of the flexible substrate for signals and grounding 106 having mesh-form patterning by boring the ground layer to have a plurality of round holes for reduced load applied to a part of the ground layer, thus letting the flexible substrate for signals and grounding 106 have flexibility, and so the load due to sharp bending at the bending part of the flexible substrate for signals and grounding 106 fixed at the backing material 107 concentrates on the boundary of the mesh shape of the ground layer, which causes a break at the ground layer unfortunately.

In order to solve the aforementioned conventional problems, one non-limiting and exemplary embodiment provides an ultrasound probe and a flexible substrate used for an ultrasound probe capable of preventing a break at the ground layer for good signal transmission.

In one general aspect, the techniques disclosed here feature:
an ultrasound probe including an ultrasound element unit, to which a flexible substrate is connected, the flexible substrate including lamination of a ground layer and a signal layer via an insulation layer. The flexible substrate may include a bending part and a flat part, the signal layer includes a linear first signal line and a linear second signal line that are adjacent to each other, and the ground layer includes a linear first ground line and a linear second ground line that are adjacent to each other at the bending part. The first signal line and the first ground line may be opposed to each other, and the second signal line and the second ground line may be opposed to each other.

In one general aspect, the techniques disclosed here also feature:

a flexible substrate used for the ultrasound probe according to one aspect of the present disclosure. The flexible substrate of the present disclosure may include lamination of a ground layer and a signal layer via an insulation layer, and a bending part and a flat part. The signal layer may include a linear first signal line and a linear second signal line that are adjacent to each other. The ground layer may include a linear first ground line and a linear second ground line that are adjacent to each other at the bending part. The first signal line and the first ground line may be opposed to each other, and the second signal line and the second ground line may be opposed to each other.

Such a configuration can prevent a break of a ground layer at a bending part of a flexible substrate and can reduce connection failure of transmission/reception signals for good signal transmission.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

The following describes embodiments of an ultrasound probe and a flexible substrate used for an ultrasound probe of the present disclosure, with reference to the drawings.

Embodiment 1

Figure 1:
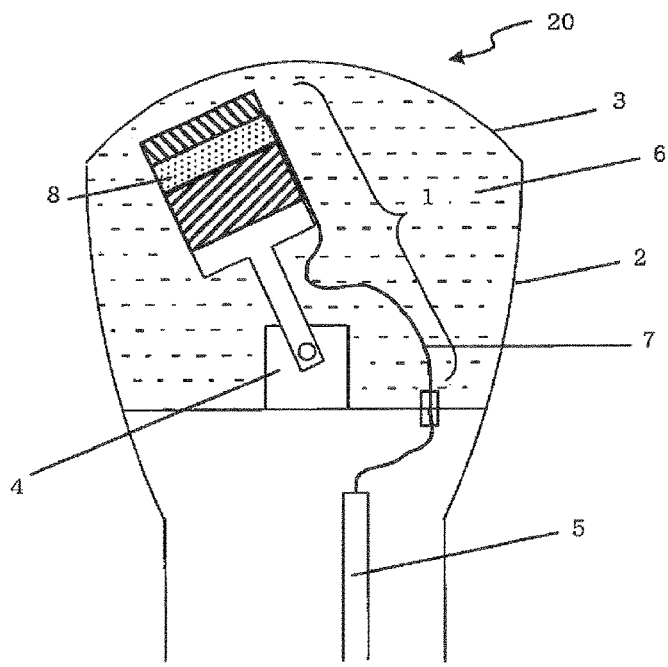
FIG. 1 schematically shows an exemplary structure of an ultrasound probe that is Embodiment 1 of the present disclosure.

FIG. 1 schematically shows the structure of an ultrasound probe that is Embodiment 1 of the present disclosure.

In FIG. 1, an ultrasound probe 20 includes: an ultrasound element unit 1 to transmit/receive ultrasound waves; an enclosure 2; an acoustic window 3 that is a part of the enclosure 2 irradiated with ultrasound waves from the ultrasound element unit 1; a swing mechanism unit 4 to mechanically swing the ultrasound element unit 1; a probe cable 5 for electrical connection between the ultrasound element unit 1 and an ultrasound diagnosis apparatus main body (not illustrated); acoustic coupling solution 6 to fill the enclosure 2; and a flexible substrate (hereinafter called a flexible substrate for signals and grounding) 7 for electrical connection between the ultrasound element unit 1 and the probe cable 5.

The ultrasound element unit 1 includes a piezoelectric element 8 that receives a driving signal from the ultrasound diagnosis apparatus main body via the probe cable 5 and the flexible substrate for signals and grounding 7, and the piezoelectric element 8 converts the driving signal into ultrasound waves. The ultrasound waves are applied to a subject via the acoustic coupling solution 6 and the acoustic window 3. Ultrasound waves reflected from the subject pass through the acoustic window 3 and the acoustic coupling solution 6, which are then received and converted into electrical signals by the piezoelectric element 8 and are sent to the ultrasound diagnosis apparatus main body for signal processing via the flexible substrate for signals and grounding 7 and the probe cable 5, whereby a two-dimensional image can be acquired.

Mechanically swinging of the ultrasound element unit 1 by the swing mechanism unit 4 including a motor or the like while acquiring two-dimensional information by the ultrasound element unit 1 allows three-dimensional information to be input/output. This three-dimensional information is processed by the ultrasound diagnosis apparatus main body, whereby a three-dimensional image can be visualized. Since the ultrasound element unit 1 swings, the flexible substrate for signals and grounding 7 has to have an allowance in the enclosure 2. To suppress a break of the flexible substrate for signals and grounding 7 due to the load during swinging, the flexible substrate for signals and grounding 7 has an arc-shape or an S-letter shape in the view of the rotary axle of the swing mechanism unit 4 from the upper face. Such an arc-shape or an S-letter shape of the flexible substrate for signals and grounding 7 removes the concentration of the load due to swinging.

Figure 2A:
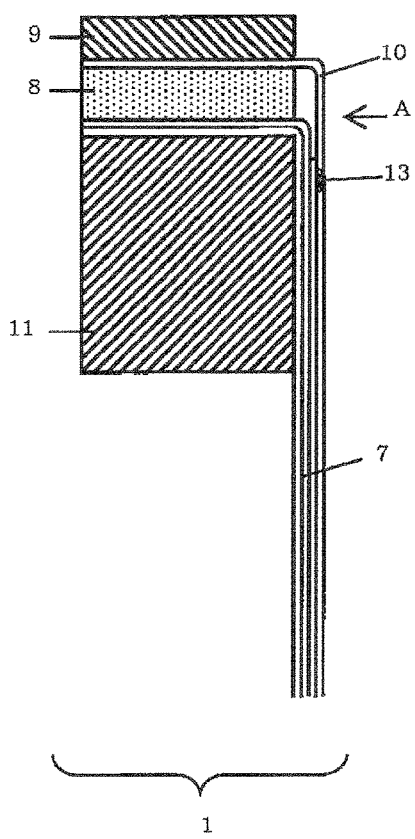
FIG. 2A schematically shows an exemplary ultrasound element unit in Embodiment 1 of the present disclosure.
Figure 2B:
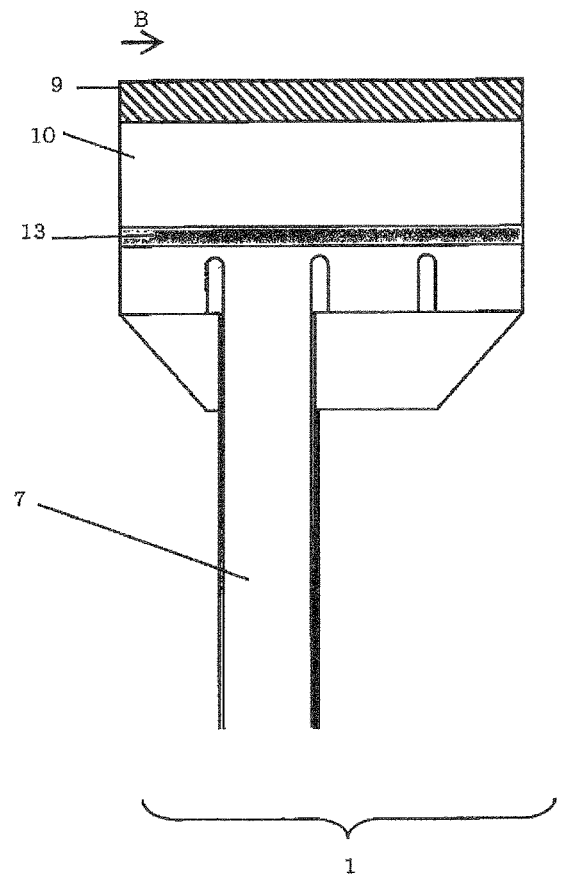
FIG. 2B schematically shows an exemplary ultrasound element unit viewed from direction A.

The following describes the above-mentioned ultrasound element unit 1 in details. FIGS. 2A and 2B schematically show the ultrasound element unit 1. FIG. 2B is a view of FIG. 2A from the direction A.

As shown in FIG. 2A, the ultrasound element unit 1 that transmits/receives ultrasound waves includes: the flexible substrate for signals and grounding 7 including a very thin (about 1 µm to 10 µm) conductor made of copper, for example, stacked on a high-polymer material such as polyimide to transmit electrical signals for transmission and reception; the piezoelectric element 8 including piezoceramic such as PZT; an acoustic matching layer 9 including at least one layer for effective transmission of ultrasound waves to an ultrasound waves emission face of the piezoelectric element 8; ground copper foil 10 attached to a negative-side electrode of the piezoelectric element 8; and a backing material 11 to hold the piezoelectric element 8 mechanically and attenuate unnecessary ultrasound signals.

A part of the flexible substrate for signals and grounding 7 is disposed at a positive-side electrode of the piezoelectric element 8 so that the part of the flexible substrate for signals and grounding 7 is sandwiched between the piezoelectric element 8 and the backing material 11.

A part of the ground copper foil 10 is disposed at the negative-side electrode of the piezoelectric element 8 so that the part of the ground copper foil 10 is sandwiched between the piezoelectric element 8 and the acoustic matching layer 9.

In this way, viewed from the side of the acoustic window 3, the ultrasound element unit 1 includes the lamination of the acoustic matching layer 9, the ground copper foil 10, the piezoelectric element 8, an I/O signal layer 7a of the flexible substrate for signals and grounding 7 and the backing material 11 in this stated order. The piezoelectric element 8 is divided into several tens to several hundreds of elements by means of dicing, for example, in the array direction (the direction of arrow B in FIG. 2B).

The positive-side and the negative-side electrodes (not illustrated) of the piezoelectric element 8 are formed by plating or sputtering of metal such as gold, silver, chrome, nickel or titanium. In another configuration, an acoustic lens (not illustrated) may be provided for focusing of ultrasound waves on the face of the acoustic matching layer 9 on the opposite side of the ground copper foil 10 stacked thereon.

Figure 3:
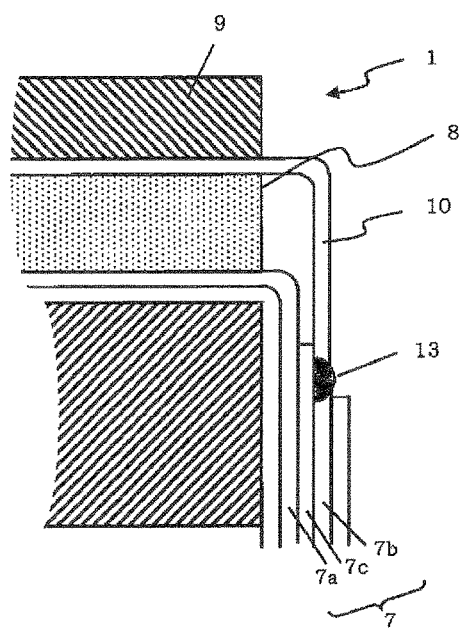
FIG. 3 shows an exemplary ultrasound element unit in Embodiment 1 of the present disclosure in details.

Referring now to FIG. 3 showing the ultrasound element unit 1 in details, the following describes the flexible substrate for signals and grounding 7. Like reference numerals in FIGS. 1, 2A and 2B refer to like parts in FIG. 3 for simplification of the description.

The flexible substrate for signals and grounding 7 includes the I/O signal layer 7a, a ground layer 7b and an insulation layer 7c. The I/O signal layer 7a and the ground layer 7b are stacked via the insulation layer 7c. The I/O signal layer 7a is stacked on the positive-side electrode of the piezoelectric element 8 only. The ground copper foil 10 attached to the negative-side electrode of the piezoelectric element 8 is electrically connected to the ground layer 7b of the flexible substrate for signals and grounding 7 at an electrical connection part 13 with solder or conductive adhesive, for example. In this way, two signal layers of the I/O signal layer 7a and the ground layer 7b making up the flexible substrate for signals and grounding 7 stick out from the piezoelectric element 8. The I/O signal layer 7a of the flexible substrate for signals and grounding 7 is formed with a linear pattern corresponding to the elements of the ultrasound element unit 1.

Figure 4:
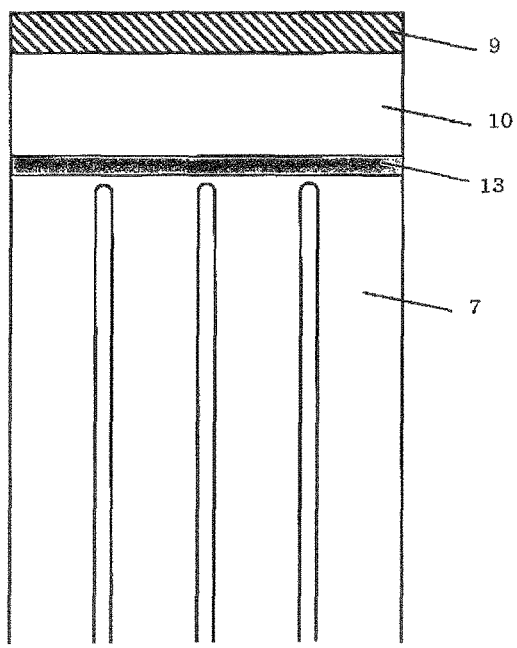
FIG. 4 schematically shows an exemplary ultrasound element unit in Embodiment 1 of the present disclosure after bonding and stacking.
Figure 5A:
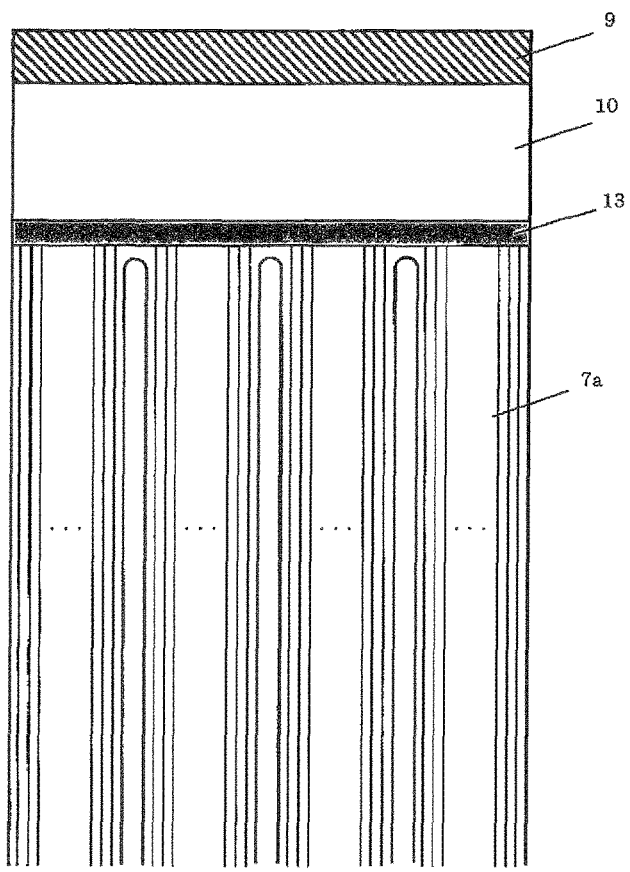
FIG. 5A is an exemplary front view of an I/O signal layer of a flexible substrate for signals and grounding in Embodiment 1 of the present disclosure.
Figure 5B:
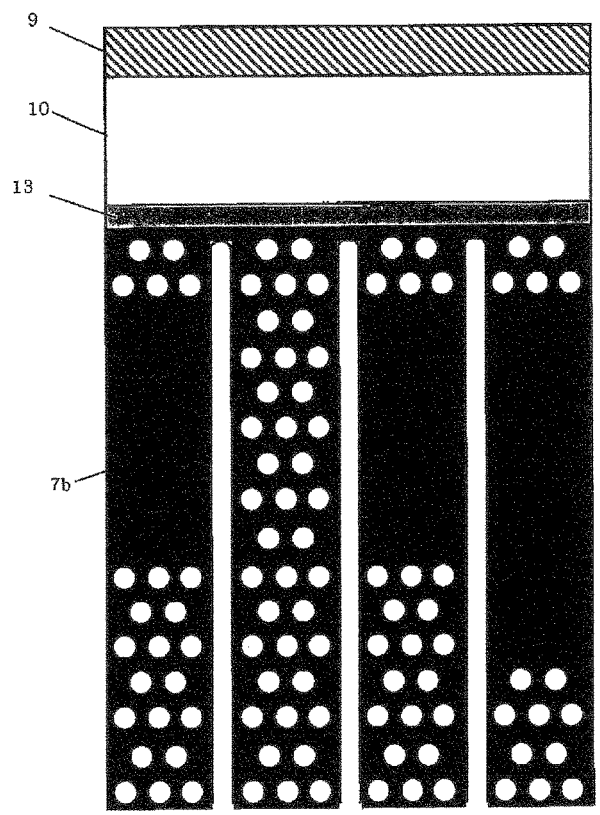
FIG. 5B is an exemplary front view of a ground layer of a flexible substrate for signals and grounding in Embodiment 1 of the present disclosure.
Figure 5C:
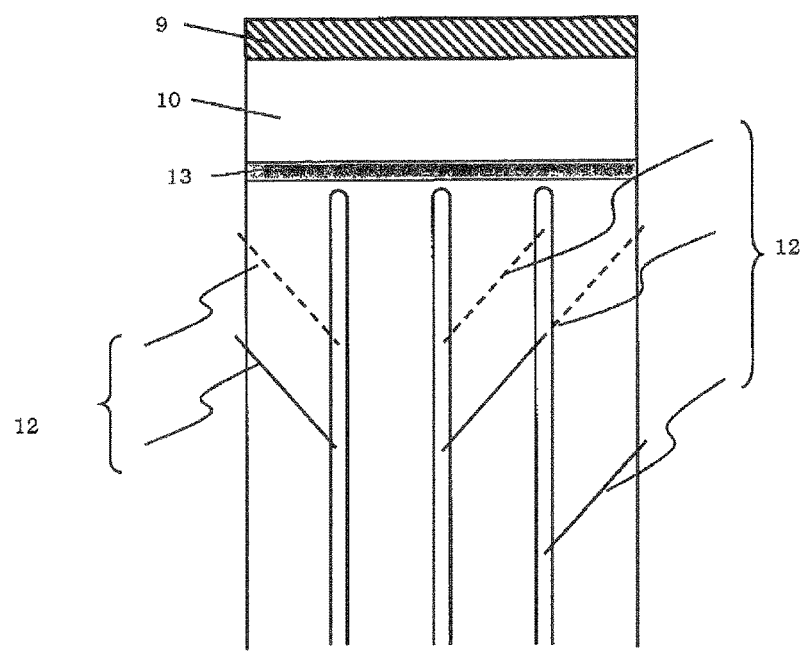
FIG. 5C is an exemplary front view of bending lines of a flexible substrate for signals and grounding in Embodiment 1 of the present disclosure.

Referring next to FIGS. 2A, 2B, 4A, 5A, 5B and 5C, the processing procedure of the ultrasound element unit 1 is described below. FIG. 4 schematically shows the ultrasound element unit 1 after bonding and stacking, and the ultrasound element unit 1 of FIG. 4 subjected to bending described later will assume the shape of the ultrasound element unit 1 of FIG. 2B. FIGS. 5A, 5B and 5C describe the processing method of the flexible substrate for signals and grounding 7 in details.

Firstly as shown in FIG. 2A, the acoustic matching layer 9, the ground copper foil 10, the piezoelectric element 8, the flexible substrate for signals and grounding 7 and the backing material 11 are stacked and bonded with epoxy-based adhesive or conductive adhesive, for example, one by one. Before bending the flexible substrate for signals and grounding 7, the ultrasound element unit 1 viewed from the same direction as the direction A of FIG. 2A is in the state of FIG. 4. Then the piezoelectric element 8 is divided into elements by dicing, for example, and division grooves may be filled with epoxy resin or silicone rubber, for example. The ground layer 7b of the flexible substrate for signals and grounding 7 makes the elements have ground signals at electrically common potential. FIG. 2B shows the state where the ground copper foil 10 and the ground layer 7b are connected via the electrical connection part 13. Instead, the ground layer 7b in the divided state into elements may be connected to the ground copper foil 10. In FIG. 4, the flexible substrate for signals and grounding 7 is divided into four blocks, which is not a limiting example.

Then, the flexible substrate for signals and grounding 7 of FIG. 4 is bent, and the four blocks are overlaid to be in the shape of FIG. 2B.

The following describes the bending processing of the flexible substrate for signals and grounding 7 in details. To this end, FIG. 5C shows the I/O signal layer 7a, the ground layer 7b and bending lines 12 of the flexible substrate for signals and grounding 7. In the following, a bending part refers to the bending lines 12 and their surroundings. A flat part refers to a part of the flexible substrate for signals and grounding 7 not subjected to bending.

In FIG. 5A, the I/O signal layer 7a is formed with a linear pattern corresponding to the elements of the ultrasound element unit 1 to the connection part with the probe cable 5. As shown in the drawing, the I/O signal layer 7a includes a plurality of linear signal lines that are elongated mutually in parallel. To suppress a break of the flexible substrate for signals and grounding 7 due to swinging load generated by swinging of the ultrasound element unit 1 in the acoustic coupling solution 6 inside the enclosure 2, the flexible substrate for signals and grounding 7 has to have flexibility. To this end, as shown in FIG. 5B, the ground layer 7b of the flexible substrate for signals and grounding 7 includes a movable part moving with mechanical swinging that has a mesh-form patterning by boring a part of the conductor to have round holes for flexibility.

In FIG. 5B, the mesh form includes round holes to let the flexible substrate for signals and grounding 7 have flexibility, and the shape or the size of the holes may be elliptical or polygonal holes, for example, to be like a perforated metal. The patterning of the mesh form in FIG. 5B includes the arrangement of a plurality of round holes, which may be arranged at regular intervals or irregular intervals. The opening ratio, representing the ratio between the area of the holes as a whole by patterning in the mesh form and the area of the conductor part of the flexible substrate for signals and grounding 7, assumed is from 5% to 95%. The patterning in the mesh form does not include holes simply bored at several parts, e.g, through holes.

As shown in FIG. 1, the flexible substrate for signals and grounding 7 as a part of the ultrasound element unit 1 mechanically swings in the enclosure 2 filled with the acoustic coupling solution 6 of FIG. 1. At this time, resistance that the flexible substrate for signals and grounding 7 receives from the acoustic coupling solution 6 during swinging has to be reduced so as to suppress the motor output from the swing mechanism unit 4. To this end, the flexible substrate for signals and grounding 7 has a small surface area, and so the flexible substrate for signals and grounding 7 is bent along the bending lines 12 of FIG. 5C to be the shape of FIG. 2B. The bending part includes a mountain fold part to be folded like a mountain and a valley fold part to be folded like a valley viewed from the ground layer 7b of the I/O signal layer 7a and the ground layer 7b that are stacked. When the ground layer 7b is above the I/O signal layer 7a in the ultrasound element unit 1 viewed from the direction A as in FIG. 2A, the dashed lines of the bending lines 12 in FIG. 5C are a valley fold part viewed from the ground layer 7b. Then, the solid lines of the bending lines 12 in FIG. 5C are a mountain fold part viewed from the ground layer 7b. Herein, after bending the flexible substrate for signals and grounding 7, dicing may be performed.

Since the ground layer 7b has mesh-form patterning, mechanical load generated from the swinging of the ultrasound element unit 1 including the bent flexible substrate for signals and grounding 7 will concentrate on the boundary of the mesh part of the ground layer 7b. This may cause a break of the ground layer 7b of the flexible substrate for signals and grounding 7. To avoid this, the ground layer 7b of the flexible substrate for signals and grounding 7 has to have a configuration to suppress such concentration of the load on the boundary of the mesh part due to bending. Since the bending part of the ground layer 7b of the flexible substrate for signals and grounding 7 is less influenced from the mechanical load due to swing, the bending part is configured to be a conductor at the entire face without having mesh-form patterning.

Such a configuration without mesh-form patterning at the bending part of the ground layer 7b of the flexible substrate for signals and grounding 7 suppresses concentration of the load due to bending on the mesh part of the ground layer 7b. This can prevent a break of the ground layer 7b of the flexible substrate for signals and grounding 7. Since the bending part of the ground layer 7b is less influenced from the mechanical load due to swinging, the flexibility of the ultrasound element unit 1 is not impaired without mesh-form patterning.

Such a configuration can prevent a break of the ground layer 7b and can reduce connection failure of transmission/reception signals for good signal transmission.

Embodiment 2

Figure 6:
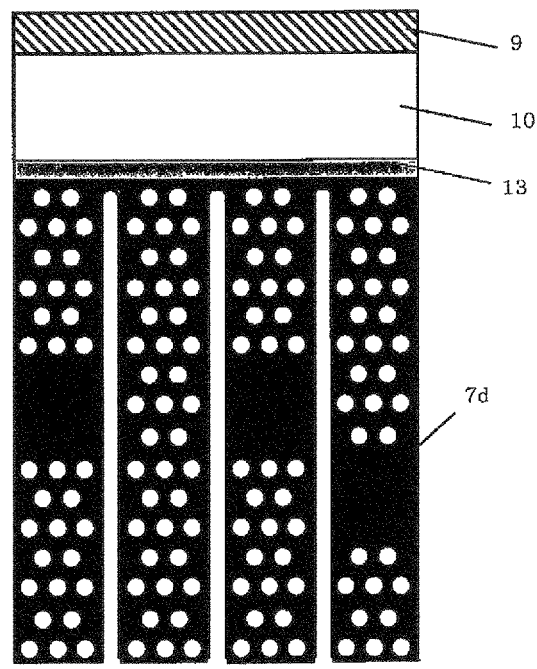
FIG. 6 is an exemplary front view of a ground layer of a flexible substrate for signals and grounding in Embodiment 2 of the present disclosure.

FIG. 6 is a front view of a ground layer 7d of a flexible substrate for signals and grounding 7 in an ultrasound probe that is Embodiment 2 of the present disclosure.

In FIG. 6, a part of the ground layer 7d corresponding to the valley fold part of the bending lines 12 of the flexible substrate for signals and grounding 7 in FIG. 5C of Embodiment 1 has a mesh-form patterning. A part corresponding to the mountain fold part of the bending lines 12 includes a conductor at the entire face similarly to Embodiment 1. An area other than the bending part has mesh-form patterning.

Similarly to the description of Embodiment 1, the mountain fold part refers to a part to be folded like a mountain and the valley fold part refers to a part to be folded like a valley viewed from the side of the ground layer 7d of the I/O signal layer 7a and the ground layer 7d stacked in the state where the ground layer 7d is located on the front side of the I/O signal layer 7a when the ultrasound element unit 1 is viewed from the direction A as in FIG. 2A.

Figure 7:
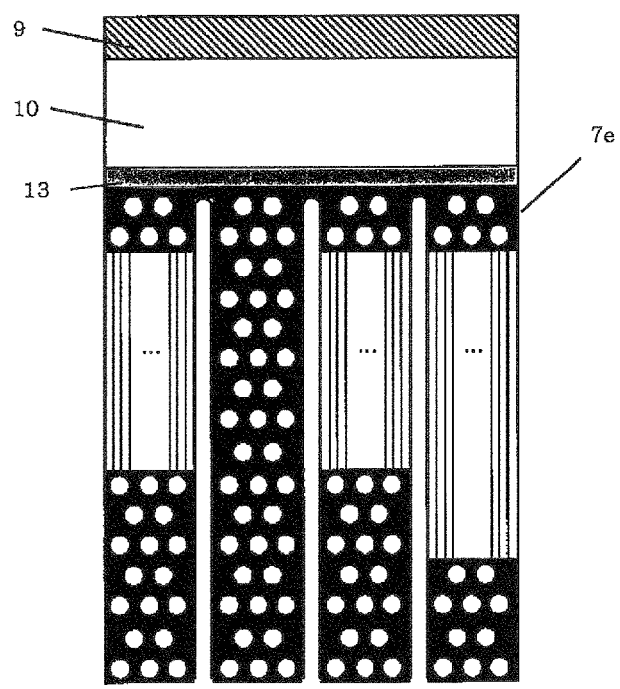
FIG. 7 is an exemplary cross-sectional view of a bending part of a flexible substrate for signals and grounding in Embodiment 2 of the present disclosure.

Referring to FIGS. 2A, 2B, 5A, 5B, 5C, 6 and 7, the following describes the reason why the mountain fold part only of the bending lines 12 of the flexible substrate for signals and grounding 7 includes a conductor at the entire face. FIG. 7 is a cross-sectional view of the bending part of the flexible substrate for signals and grounding 7 after the ultrasound element unit 1 is bent as in FIG. 2B. FIG. 7 shows one of the mountain fold parts of a plurality of bending lines of the flexible substrate for signals and grounding 7 of FIG. 5C that is simplified for illustration. The I/O signal layer 7a and the ground layer 7d are stacked via an insulation layer 7c.

At the bending part of FIG. 7, the ground layer 7d located outside of the layers of the bent flexible substrate for signals and grounding 7 is extended more to be longer than the I/O signal layer 7a located inside. This means that the ground layer 7d of the flexible substrate for signals and grounding 7 at the bending part having mesh-form patterning may generate a break because load due to the bending concentrates on the boundary of the mesh part of the ground layer 7d.

To avoid this, a mountain fold part in FIG. 6 viewed from the ground layer 7d of the bending lines 12 at the flexible substrate for signals and grounding 7 in FIG. 5C is not provided with mesh-form patterning to be a conductor at the entire face. As a result, in the state where the ground layer 7d is located outside of the layers of the bent flexible substrate for signals and grounding 7, the load due to bending becomes uniform. That is, since the ground layer 7d does not have mesh-form patterning at the mount fold part, the ground layer 7d does not generate a break. A valley fold part viewed from the ground layer of the bending lines 12 at the flexible substrate for signals and grounding 7 in FIG. 5C includes the I/O signal layer 7a located outside of the layers of the flexible substrate for signals and grounding 7 and the ground layer 7d located inside, and the outside I/O signal layer 7a, even in the more extended direction, does not lead to a break because it has a linear shape. Therefore when a plurality of blocks of the flexible substrate for signals and grounding 7 are overlaid, a part of the flexible substrate for signals and grounding 7 where the inside layer at the bending part is the ground layer 7d may include mesh-form patterning at the ground layer.

Such a configuration can prevent a break of the ground layer 7d simply by changing a pattern at a part of the ground layer 7d and can reduce connection failure of transmission/reception signals for good signal transmission.

Embodiment 3

Embodiment 3 is different from Embodiment 1 in the patterning shape of the ground layer at the flexible substrate for signals and grounding 7, and other configuration is the same as Embodiment 1. Like reference numerals in Embodiment 1 refer to like parts in the following to omit their descriptions.

Figure 8:
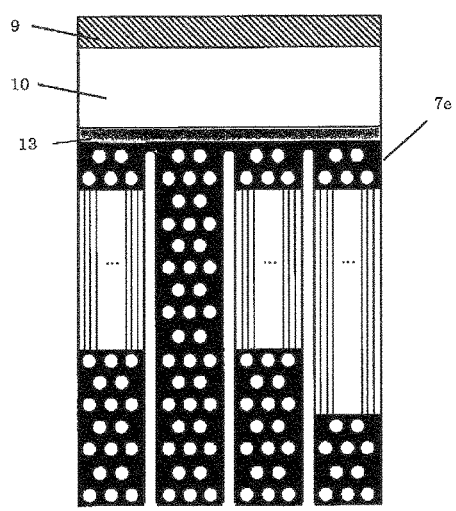
FIG. 8 is an exemplary front view of a ground layer of a flexible substrate for signals and grounding in Embodiment 3 of the present disclosure.

FIG. 8 is a front view of a ground layer 7e of a flexible substrate for signals and grounding 7 in an ultrasound probe that is Embodiment 3 of the present disclosure.

FIG. 8 shows an ultrasound probe according to Embodiment 3, corresponding to FIG. 5B of Embodiment 1. Similarly to FIG. 5A, an I/O signal layer 7a of the flexible substrate for signals and grounding 7 includes a plurality of linear signal lines that are elongated mutually in parallel to a connection part with the probe cable 5. As shown in FIG. 8, the ground layer 7e includes a plurality of linear ground lines that are elongated mutually in parallel at a part where the bending lines 12 exist in FIG. 5C. The ground layer 7e includes a flat part that is not bent, having mesh-form patterning by boring a part of a conductor to have round holes, thus letting the flexible substrate for signals and grounding 7 have flexibility. The ground layer 7e at the flat part may be configured to cover a plurality of signal lines instead of having mesh-form patterning. Alternatively, as in the ground layer 7b at the bending part of FIG. 5B, the ground layer may be configured to include a conductor at the entire face over the entire signal lines.

Figure 9:
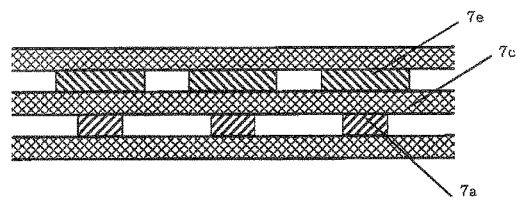
FIG. 9 is an exemplary cross-sectional view of a flexible substrate for signals and grounding in Embodiment 3 of the present disclosure in the stacking direction.

FIG. 9 is a cross-sectional view of the flexible substrate for signals and grounding 7 at the bending part in the stacking direction. On the I/O signal layer 7a including a plurality of linear signal lines is stacked an insulation layer 7c, on which the ground layer 7e including a plurality of linear ground lines is stacked. At a top layer and a bottom layer of the lamination are formed protective insulation films to protect the I/O signal layer 7a and the ground layer 7e. As shown in FIG. 9, one ground line is disposed above one signal line so as to be opposed to each other, where one ground line opposed and stacked covers one signal line via the insulation layer 7c. The insulation layer 7c is continuously formed across the adjacent two signal lines. One ground line has a width wider than a width of the opposed one signal line.

In the case of the ground layer 7e at the bending part having a mesh form, mechanical load generated from bending of the flexible substrate for signals and grounding 7 may concentrate on the boundary of the mesh part of the ground layer 7e and cause a break in the ground layer 7e. The configuration of the present embodiment has a function to suppress such concentration of the load on the ground layer 7e because the I/O signal layer 7a and the ground layer 7e are located on the same line in the stacking direction of the flexible substrate for signals and grounding 7, meaning uniform mechanical load due to bending. Since the ground lines have a wider width than the I/O signal lines, the concentration of the load on the ground layer 7e further can be suppressed. Compared with the configuration including the ground layer 7e including a conductor at the entire face at the bending part, the area of the conductor becomes small, and so the flexible substrate for signals and grounding 7 has excellent flexibility.

In FIG. 8, the mesh form includes round holes to let the flexible substrate for signals and grounding 7 have flexibility, and the shape or the size of the holes may be elliptical or polygonal holes, for example, to be like a perforated metal. The patterning of the mesh form in FIG. 8 includes the arrangement of a plurality of round holes, which may be arranged at regular intervals or irregular intervals. The opening ratio, representing the ratio between the area of the holes as a whole by patterning in the mesh form and the area of the conductor part of the flexible substrate for signals and grounding 7, assumed is from 5% to 95%.

Such a configuration can prevent a break of the ground layer 7e and can reduce connection failure of transmission/reception signals for good signal transmission.

Embodiment 4

Embodiment 4 is different from Embodiment 3 in the patterning shape of the ground layer at the flexible substrate for signals and grounding 7, and other configuration is the same as Embodiment 3. Like reference numerals in Embodiment 3 refer to like parts in the following to omit their descriptions.

Figure 10:
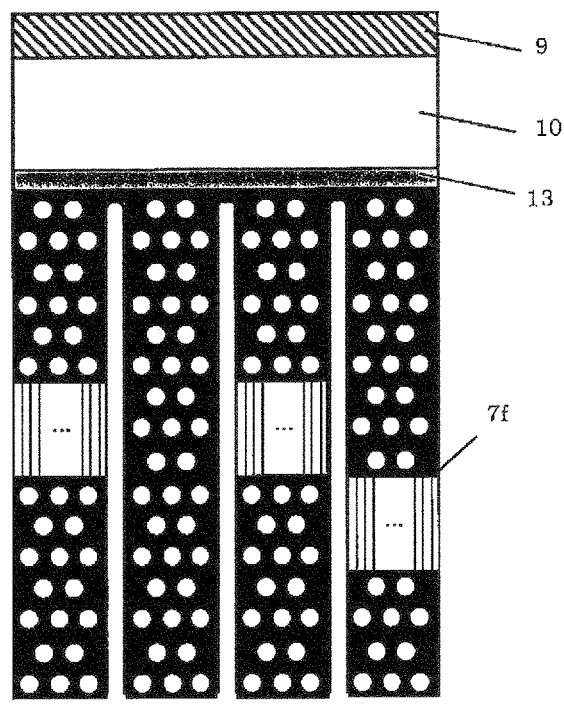
FIG. 10 is an exemplary front view of a ground layer of a flexible substrate for signals and grounding in Embodiment 4 of the present disclosure.

FIG. 10 is a front view of a ground layer 7f of a flexible substrate for signals and grounding 7 in an ultrasound probe that is Embodiment 4 of the present disclosure.

The drawing showing bending parts of the flexible substrate for signals and grounding 7 in Embodiment 4 is similar to FIG. 5C. In FIG. 10, a part of a ground layer 7f corresponding to the valley fold part of the bending lines 12 of the flexible substrate for signals and grounding 7 in FIG. 5C has a mesh-form patterning. A part of the ground layer 7f corresponding to the mountain fold part of the bending lines 12 includes a plurality of linear ground lines elongated mutually in parallel similarly to Embodiment 3. A part other than the bending part, i.e., the flat part has mesh-form patterning. The flat part and the valley fold part of the ground layer 7f may be configured to cover a plurality of signal lines instead of having mesh-form patterning. Alternatively, the ground layer may be configured to include a conductor at the entire face over the entire signal lines. Similarly to the description of Embodiment 1, the valley fold part and the mountain fold part are a mountain fold part to be folded like a mountain and a valley fold part to be folded like a valley viewed from the side of the ground layer 7f between the I/O signal layer 7a and the ground layer 7f that are stacked in the state where the ground layer 7f is located on the front side of the I/O signal layer 7a when the ultrasound element unit 1 is viewed from the direction A in FIG. 2A.

FIG. 9 is a cross-sectional view of the flexible substrate for signals and grounding 7 at a mountain fold part in the stacking direction, where the ground layer 7e is to be read as the ground layer 7f. On the I/O signal layer 7a including a plurality of linear signal lines is stacked an insulation layer 7c, on which the ground layer 7f including a plurality of linear ground lines is stacked. At a top layer and a bottom layer of the lamination are formed protective insulation films to protect the I/O signal layer 7a and the ground layer 7f. As shown in FIG. 9, one ground line is disposed above one signal line so as to be opposed to each other, where one ground line opposed and stacked covers one signal line via the insulation layer 7c. The insulation layer 7c is continuously formed across the adjacent two signal lines. One ground line has a width wider than a width of the opposed one signal line.

In the case of the ground layer 7f at the mountain fold part having a mesh form, mechanical load generated from bending of the flexible substrate for signals and grounding 7 may concentrate on the boundary of the mesh part of the ground layer 7f and cause a break in the ground layer 7f. The configuration of the present embodiment has a function to suppress such concentration of the load on the ground layer 7f because the I/O signal layer 7a and the ground layer 7f are located on the same line in the stacking direction of the flexible substrate for signals and grounding 7, meaning uniform mechanical load due to bending. Since the ground lines have a wider width than the I/O signal lines, the concentration of the load on the ground layer 7f further can be suppressed. Compared with the configuration including the ground layer 7f including a conductor at the entire face at the bending part, the area of the conductor becomes small, and so the flexible substrate for signals and grounding 7 has excellent flexibility.

In FIG. 8, the mesh form includes round holes to let the flexible substrate for signals and grounding 7 have flexibility, and the shape or the size of the holes may be elliptical or polygonal holes, for example, to be like a perforated metal. The patterning of the mesh form in FIG. 8 includes the arrangement of a plurality of round holes, which may be arranged at regular intervals or irregular intervals. The opening ratio, representing the ratio between the area of the holes as a whole by patterning in the mesh form and the area of the conductor part of the flexible substrate for signals and grounding 7, assumed is from 5% to 95%.

Referring to FIGS. 2A, 2B, 5A, 5B, 5C, 7 and 10, the following describes the reason why the mountain fold part only of the bending lines 12 of the flexible substrate for signals and grounding 7 includes linear ground lines. In Embodiment 4, the ground layer 7b in FIGS. 5A and 5B is read as the ground layer 7f, and the ground layer 7d in FIG. 7 is read as the ground layer 7f. FIG. 7 is a cross-sectional view of the bending part of the flexible substrate for signals and grounding 7 after the ultrasound element unit 1 is bent as in FIG. 2B. FIG. 7 shows one of the mountain fold parts of a plurality of bending lines 12 of the flexible substrate for signals and grounding 7 of FIG. 5C that is simplified for illustration. The I/O signal layer 7a and the ground layer 7f are stacked via an insulation layer 7c.

At the bending part of FIG. 7, the ground layer 7f located outside of the layers of the bent flexible substrate for signals and grounding 7 is extended more to be longer than the I/O signal layer 7a located inside. This means that the ground layer 7f of the flexible substrate for signals and grounding 7 at the bending part having a mesh-form patterning may generate a break because load due to the bending concentrates on the boundary of the mesh part of the ground layer 7f.

To avoid this, a mountain fold part in FIG. 10 viewed from the ground layer 7f of the bending lines 12 at the flexible substrate for signals and grounding 7 in FIG. 5C is provided with linear ground lines instead of having mesh-form patterning. As a result, in the state where the ground layer 7f is located outside of the layers of the bent flexible substrate for signals and grounding 7, the load due to bending becomes uniform. That is, since the ground layer 7f does not have mesh-form patterning at the mount fold part, the ground layer 7f does not generate a break. A valley fold part viewed from the ground layer of the bending lines 12 at the flexible substrate for signals and grounding 7 in FIG. 5C includes the I/O signal layer 7a located outside of the layers of the flexible substrate for signals and grounding 7 and the ground layer 7f located inside, and the outside I/O signal layer 7a, even in the more extended direction, does not lead to a break because it has a linear shape. Therefore when a plurality of blocks of the flexible substrate for signals and grounding 7 are overlaid, a part of the flexible substrate for signals and grounding 7 where the inside layer at the bending part is the ground layer 7f may include mesh-form patterning at the ground layer.

Such a configuration can prevent a break of the ground layer 7f simply by changing a pattern at a part of the ground layer 7f and can reduce connection failure of transmission/reception signals for good signal transmission.

Embodiment 5

Embodiment 5 is different from Embodiments 1 to 4 in that a flexible substrate 7 of an ultrasound probe has a mark indicating a bending part, but is the same in other configuration. Embodiment 5 can be combined with any of Embodiments 1 to 4.

Figure 11:
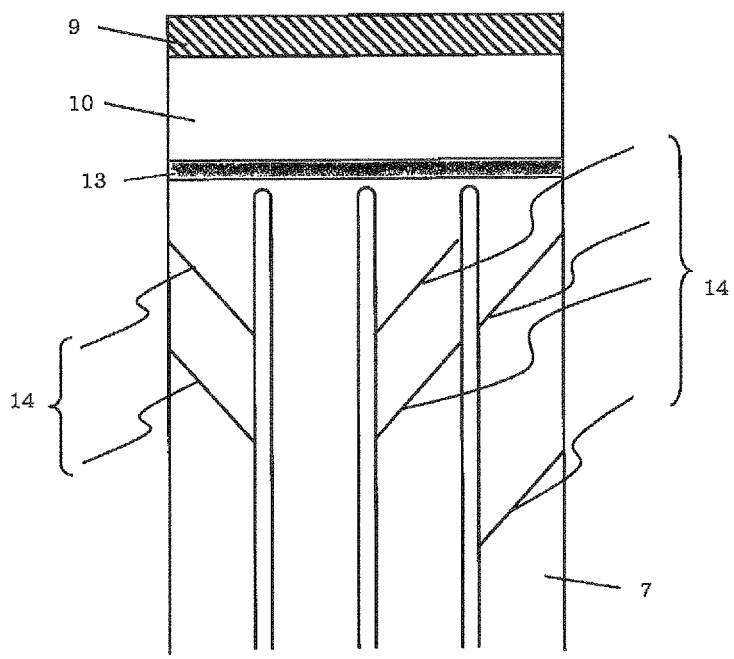
FIG. 11 is an exemplary front view of an insulation layer of a flexible substrate for signals and grounding in Embodiment 5 of the present disclosure.
Figure 12:
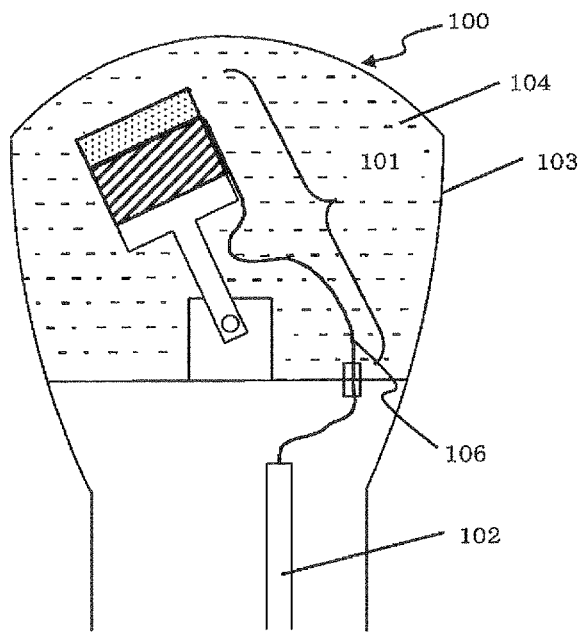
FIG. 12 schematically shows exemplary configuration of a conventional ultrasound probe.
Figure 13:
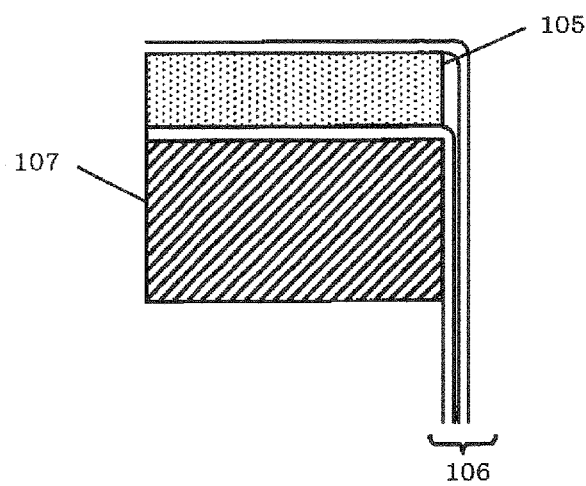
FIG. 13 schematically shows an ultrasound element unit of a conventional ultrasound probe.

FIG. 11 is a front view of an insulation layer 7c between an I/O signal layer 7a and a ground layer 7b, 7d or 7e of a flexible substrate for signals and grounding 7 in an ultrasound probe that is Embodiment 5 of the present disclosure. The flexible substrate 7 includes a mark 14 for visual checking of the position of bending lines 12 at a bending part. The mark 14 clearly shows the positions corresponding to the bending lines 12 of FIG. 5 at the insulation layer 7c. Exemplary means to clearly show the mark 14 includes means to roughen the surface of the insulation layer 7c by laser processing or chemical treatment such as etching, means to apply ink very thin (e.g., several microns) or means for coloring.

The mark 14 may be formed at any one of a face of the insulation layer 7c on the side of the I/O signal layer 7a and a face on the ground layer 7b, 7d or 7e, or at both of these faces. The mark 14 may be formed at the protective insulation films at the top and bottom of the lamination of the I/O signal layer 7a and the ground layer 7b.

As described in Embodiment 1, the flexible substrate for signals and grounding 7 is bent to overlay four blocks in the form shown in FIG. 2B. At this time, the bending is performed using the mark 14, whereby the bending can be performed more easily and precisely.

The mark 14 may have a width that is visually distinguishable, which is about 0.5 mm to 2 mm, for example. The mark 14 may be a linear shape or a dot shape, or may be an elliptical or polygonal shape.

Such a configuration enables precise recognition of the bending position of the flexible substrate for signals and grounding 7, thus facilitating the bending.

In the ultrasound probe according to one aspect of the present disclosure, the ground layer may include a part which is continuously formed at the flat part from above the first signal line to above the second signal line.

In the ultrasound probe according to one aspect of the present disclosure, the insulation layer between the signal layer and the ground layer may be continuously formed at the bending part from above the first signal line to above the second signal line.

In the ultrasound probe according to one aspect of the present disclosure, the first signal line may have a width smaller than a width of the first ground line.

In the ultrasound probe according to one aspect of the present disclosure, the bending part may include a mountain fold part to be folded like a mountain and a valley fold part to be folded like a valley viewed from a side of the ground layer of the ground layer and the signal layer that are stacked, and the first ground line and the second ground line may be located at the mountain fold part.

In the ultrasound probe according to one aspect of the present disclosure, the ground layer may be continuously formed at the valley fold part from above the first signal line to above the second signal line.

In the ultrasound probe according to one aspect of the present disclosure, the flexible substrate may include a mark to enable visual checking of a bending position at the bending part.

In the ultrasound probe according to one aspect of the present disclosure, the mark may be inscribed at the insulation layer.

In the ultrasound probe according to one aspect of the present disclosure, the ground layer may have mesh-form patterning at the flat part.

In the ultrasound probe according to one aspect of the present disclosure, the bending part may include a mountain fold part to be folded like a mountain and a valley fold part to be folded like a valley viewed from a side of the ground layer of the ground layer and the signal layer that are stacked, and the ground layer at a part to be the valley fold part may have mesh-form patterning.

As stated above, the present disclosure relates to an ultrasound probe including a flexible substrate having a ground layer, a part of which has linear patterning, and such a flexible substrate used for an ultrasound probe, and is effective as an ultrasound probe and a flexible substrate used for an ultrasound probe capable of preventing a break at the ground layer and so reducing connection failure of transmission/reception signals for good signal transmission.

The invention claimed is:

1. An ultrasound probe including an ultrasound element unit, to which a flexible substrate is connected, the flexible substrate including a lamination of a ground layer and a signal layer via an insulation layer, wherein:
the flexible substrate includes a bending part and a flat part,
the flexible substrate is divided into a plurality of blocks, which are divided from each other,
the plurality of blocks of the flexible substrate are overlaid on each other such that the flexible substrate is folded to be overlaid on itself at the bending part,
the signal layer includes a linear first signal line and a linear second signal line, which, in a state before the flexible substrate is folded, are adjacent to each other and parallel to each other,
the ground layer includes a linear first ground line and a linear second ground line, which, in the state before the flexible substrate is folded, are adjacent to each other and parallel to each other,
the first signal line and the first ground line are opposed to each other in a lamination direction at the bending part, and
the second signal line and the second ground line are opposed to each other in the lamination direction at the bending part.

2. The ultrasound probe according to claim 1, wherein the ground layer includes a part which is continuously formed at the flat part from above the first signal line to above the second signal line.

3. The ultrasound probe according to claim 1, wherein the insulation layer between the signal layer and the ground layer is continuously formed at the bending part from above the first signal line to above the second signal line.

4. The ultrasound probe according to claim 1, wherein the first signal line has a width smaller than a width of the first ground line.

5. The ultrasound probe according to claim 1, wherein:
the flexible substrate is folded to be overlaid on itself at the bending part by a fold that is concave from a point of view of the ground layer, at a first part of the bending part, and by a fold that is convex from the point of view of the ground layer, at a second part of the bending part, and
the first ground line and the second ground line are located at the second part of the bending part.

6. The ultrasound probe according to claim 5, wherein the ground layer is continuously formed at the first part of the bending part from above the first signal line to above the second signal line.

7. The ultrasound probe according to claim 1, wherein the flexible substrate includes a mark to enable visual checking of a bending position at the bending part.

8. The ultrasound probe according to claim 7, wherein the mark is inscribed at the insulation layer.

9. The ultrasound probe according to claim 1, wherein the ground layer has mesh-form patterning at the flat part.

10. The ultrasound probe according to claim 1, wherein:
the flexible substrate is folded to be overlaid on itself at the bending part by a fold that is concave from a point of view of the ground layer, at a first part of the bending part, and by a fold that is convex from the point of view of the ground layer, at a second part of the bending part, and
the ground layer has mesh-form patterning at the first part of the bending part.

11. A flexible substrate configured to be used for an ultrasound probe including an ultrasound element unit to which the flexible substrate is connected, the flexible substrate comprising:
a lamination of a ground layer and a signal layer via an insulation layer,
wherein:
the flexible substrate has a bending part and a flat part,
the flexible substrate is divided into a plurality of blocks, which are divided from each other, and which are configured to be overlaid on each other such that the flexible substrate is foldable to be overlaid on itself at the bending part,
the signal layer includes a linear first signal line and a linear second signal line that are adjacent to each other and parallel to each other,
the ground layer includes a linear first ground line and a linear second ground line that are adjacent to each other and parallel to each other,
the first signal line and the first ground line are opposed to each other in a lamination direction at the bending part,
the second signal line and the second ground line are opposed to each other in the lamination direction at the bending part, and
gaps are provided between the first signal line and the second signal line, and between the first ground line and the second ground line.

* * * * *